(12) United States Patent
Nysæther et al.

(10) Patent No.: US 8,465,292 B2
(45) Date of Patent: Jun. 18, 2013

(54) SYSTEM AND METHOD FOR INCREASED ACCURACY IN DETERMINING CPR CHEST COMPRESSION DEPTH IN REAL TIME

(75) Inventors: Jon Nysæther, Hafrsfjord (NO); Joar Eilevstjønn, Sandnes (NO)

(73) Assignee: Laerdal Medical AS, Stavanger (NO)

( * ) Notice: Subject to any disclaimer, the term of this patent is extended or adjusted under 35 U.S.C. 154(b) by 1300 days.

(21) Appl. No.: 12/032,574

(22) Filed: Feb. 15, 2008

(65) Prior Publication Data

US 2008/0208082 A1 Aug. 28, 2008

(30) Foreign Application Priority Data

Feb. 15, 2007 (GB) .................................. 0702969.7

(51) Int. Cl.
*G09B 23/28* (2006.01)
*A61B 5/00* (2006.01)

(52) U.S. Cl.
USPC .......................................... 434/265; 600/587

(58) Field of Classification Search
USPC .................. 600/587, 595, 529, 534; 434/262, 434/265; 601/41–44
See application file for complete search history.

(56) References Cited

U.S. PATENT DOCUMENTS

| 6,306,107 | B1 | 10/2001 | Myklebust et al. | 600/587 |
| 7,118,542 | B2 | 10/2006 | Palazzolo et al. | 601/41 |
| 7,220,235 | B2 * | 5/2007 | Geheb et al. | 601/41 |
| 2004/0082888 | A1 | 4/2004 | Palazzolo et al. | 601/41 |
| 2004/0210170 | A1 * | 10/2004 | Palazzolo et al. | 601/41 |
| 2005/0101889 | A1 * | 5/2005 | Freeman et al. | 601/41 |
| 2006/0247560 | A1 | 11/2006 | Halperin et al. | 601/41 |
| 2007/0282212 | A1 * | 12/2007 | Sierra et al. | 600/529 |

FOREIGN PATENT DOCUMENTS

| EP | 1 057 451 A2 | 12/2000 |
| WO | 00/27464 | 5/2000 |
| WO | 2004/037154 A3 | 5/2004 |
| WO | 2005/046431 A3 | 5/2005 |

OTHER PUBLICATIONS

Aase, Sven O. et al., "Compression Depth Estimation for CPR Quality Assessment Using DSP on Accelerometer Signals", IEEE Transactions on Biomechanical Engineering, vol. 49, No. 3, Mar. 2002, pp. 263-268.

* cited by examiner

*Primary Examiner* — Brian Szmal
*Assistant Examiner* — H. Q. Nguyen
(74) *Attorney, Agent, or Firm* — Dorsey & Whitney LLP

(57) ABSTRACT

Embodiments of the present invention are directed toward a system and method of determining real time chest compression depth of a CPR patient or manikin from acceleration and a reference signal, such as force. In one embodiment, an acceleration signal is filtered and integrated to determine a raw depth signal. A force signal is adjusted to having a similar amplitude, phase, and shape as the raw depth signal. The force signal is filtered. The adjusted force signal is subtracted from the filtered force signal to obtain a compensation signal. The chest compression depth is obtained by adding the raw depth signal to the compensation signal.

22 Claims, 4 Drawing Sheets

SYSTEM AND METHOD FOR INCREASED ACCURACY IN DETERMINING CPR CHEST COMPRESSION DEPTH IN REAL TIME

CROSS-REFERENCE TO RELATED APPLICATION

This application claims the benefit of United Kingdom Application No. 0702969.7, filed Feb. 15, 2007. The entire disclosure of the prior application is considered to be part of the disclosure of the instant application and is hereby incorporated by reference therein.

TECHNICAL FIELD

This invention relates to cardiopulmonary resuscitation (CPR), and more specifically to a system and method to determine chest compression depth during CPR based on an acceleration signal and a reference signal.

BACKGROUND OF THE INVENTION

CPR (Cardiopulmonary Resuscitation) feedback systems have recently gained attention as a method for improving the quality of CPR on a cardiac arrest victim. One typical feature of such systems is to measure the compression depth and rate during chest compressions, compare these with accepted guideline limits, and give verbal or visual feedback to the rescuer. For instance, the CPR feedback system could provide feedback when the compression depth does not meet the accepted value of 3.8-5.1 cm.

A system for giving feedback on compressions typically consists of a sensor pad to be placed on the victim's chest. The sensor pad may contain an accelerometer and optionally a force sensor. The compression depth measurement is usually based on double integration of acceleration. However, if not all zero offset is removed from the acceleration signal prior to double integration, the integration is likely to "run off" and the estimated depth will not be useable for giving feedback.

One approach that has been used to remove zero offset from the acceleration signal before double integration to obtain chest compression depth is disclosed in U.S. Pat. No. 6,306,107 to Myklebust et al. The method includes resetting the depth and velocity to zero each time a force switch is activated at the onset of a new compression.

Another approach described in "Compression Depth Estimation for CPR Quality Assessment Using DSP on Accelerometer Signals," IEEE Transactions on Biomechanical Engineering, Vol. 49, No. 3, March 2002, Aase et al., describes a method where the offset in acceleration is removed after each compression, by setting the boundary conditions so that the chest is assumed to return to the same position and speed when the force is released. The integration limits determining the boundary conditions are determined by the help of a force switch. The disadvantage of this method is that the method does not provide a real-time, sample-by-sample assessment of depth, but only calculates depth of the previous compression.

A more recent technique, described in U.S. Pat. No. 7,118,542 to Palazzolo et al., incorporated herein by reference in its entirety, describes a method of filtering and integrating acceleration to obtain depth. A moving average of past starting points is used to estimate the starting point of each compression. Additionally, an independent reference signal, such as an ECG (Electrocardiogram) signal with compression artifacts, may be used to assist in determining the starting points. Various types of noise reference signals may be used to estimate and remove sources of noise in the acceleration signal prior to integration, by correlating the noise reference signals with the acceleration signal.

One disadvantage with the method described in U.S. Pat. No. 7,118,542 is that it does not compensate the acceleration or depth signals for the distortion caused by the filters. In general, filters not only remove frequencies outside their pass-band, but also attenuates or delays certain frequency components within the pass-band. This may cause distortion of the filtered signal relative to the original signal.

For instance, if a high-pass filter is used to remove drift in an acceleration offset, the filter will also distort frequencies in the vicinity of its cut-off frequency. Upon double integration, these distortions will also cause distortion of the resulting depth signal. If the cut-off frequency of the filter is too close to the compression frequency, the depth signal may be significantly distorted. On the other hand, the lower the cut-off frequency, the less effective the filter will be in removing drift.

Therefore, there is a need to reduce the effects of filter distortion on the compression depth signal, while maintaining an adequate removal of sensor drift.

SUMMARY OF THE INVENTION

The present invention is directed toward a system and method of determining real time chest compression depth of a CPR patient or manikin from acceleration and a reference signal, such as force. In one aspect of the invention a method of determining chest compression depth during CPR comprises receiving a signal representing an acceleration value of the chest compression, applying one or more filters to the acceleration signal, and applying double integration on the filtered acceleration signal. In addition, the method further includes receiving and adjusting an independent reference signal to produce an adjusted reference signal and applying one or more filters to the adjusted reference signal. A compensation signal is obtained by subtracting the filtered adjusted reference signal from the adjusted reference signal. Finally, the compression depth is determined by adding the double integrated filtered acceleration signal and the compensation signal.

In another aspect of the invention, a system for determining real time chest compression depth on a patient or manikin during CPR comprises an accelerometer operable to measure an acceleration of the chest compression of the patient or manikin and generate an acceleration signal, a force sensor operable to measure compression force and generate a force signal, and a processor operable to receive the acceleration signal and the force signal. The processor being further operable to filter and integrate the acceleration signal, and adjust and filter the force signal. In addition, the processor being operable to calculate a compensation signal from the filtered and integrated acceleration signal and the adjusted and filtered force signal. Finally, the processor operable to calculate the chest compression depth from the compensation signal and the filtered and integrated acceleration signal.

DETAILED DESCRIPTION OF PREFERRED EMBODIMENTS

Embodiments of the present invention are directed toward a system and method of determining real time chest compression depth of a CPR patient or manikin from acceleration and a reference signal, such as force. Certain details are set forth below to provide a sufficient understanding of the embodiments of the invention. However, it will be clear to one skilled in the art that various embodiments of the invention may be practiced without these particular details.

One embodiment of the invention involves the calculation of real time chest compression depth by adding a compensation signal to a raw compression depth signal. The raw compression depth signal is obtained by filtering and integrating a waveform to reduce the effects of filter distortion, while maintaining adequate removal of sensor drift. The compensation signal is determined by adjusting an independent reference signal to have a similar amplitude, shape, and phase as the raw compression depth signal. The adjusted signal is filtered. In one embodiment, the filters used to remove the offset drift in the acceleration signal are the same filters used to filter the adjusted reference signal. The compensation signal, which is equal to the difference between the adjusted reference signal and the filtered reference signal, is calculated and added to the raw compression depth signal to compensate for the distortion caused by the filters. The compensation signal is presumed to be approximately equal to the portion of the raw compression depth signal removed by the filter, thus giving a more accurate determination of the actual compression depth.

Figure 1:
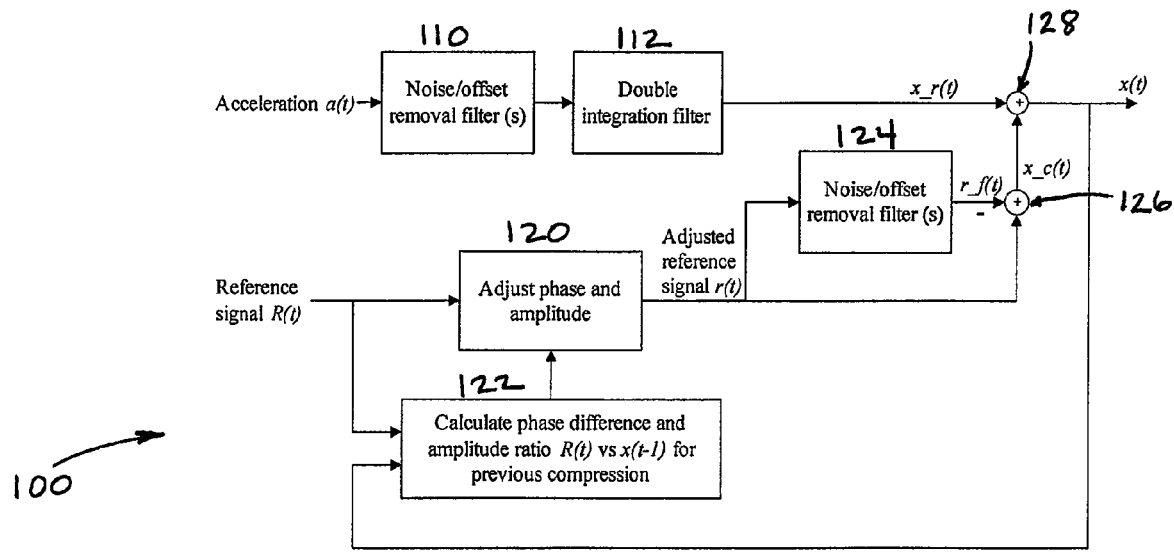
FIG. 1 is a flow chart describing a method determining chest compression depth x according to one embodiment of the invention.

FIG. 1 is a flow chart 100 describing a method for accurately determining real time chest compression depth x exercised on a patient or manikin by a CPR performer according to one embodiment of the invention. An accurate determination of the compression depth waveform x(t) as a function of time is given by the relation:

$$x(t) = x\_r(t) + x\_c(t),$$

where x_r(t) is a raw depth signal, and x_c (t) is a compensation signal.

Figure 2A:
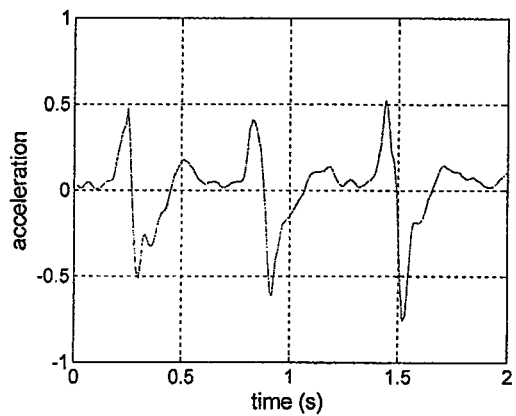
FIG. 2a shows a typical waveform of a measured acceleration signal according to an embodiment of the invention.
Figure 2B:
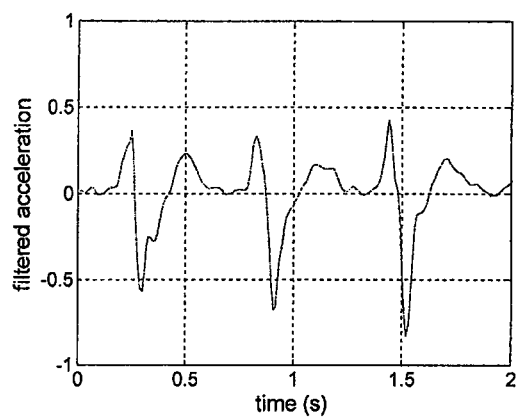
FIG. 2b shows the waveform of the acceleration signal in FIG. 2a filtered by a comb filter according to an embodiment of the invention.
Figure 2C:
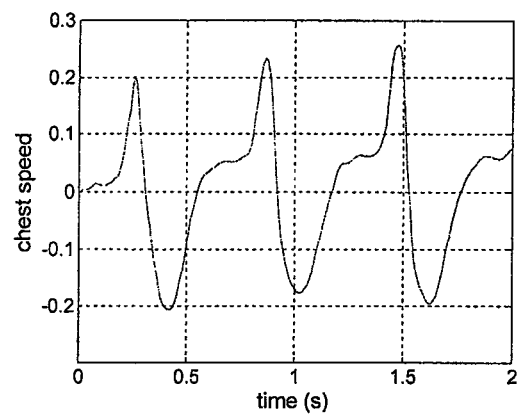
FIG. 2c shows the waveform of chest speed found by integrating the filtered acceleration signal according to an embodiment of the invention.
Figure 2D:
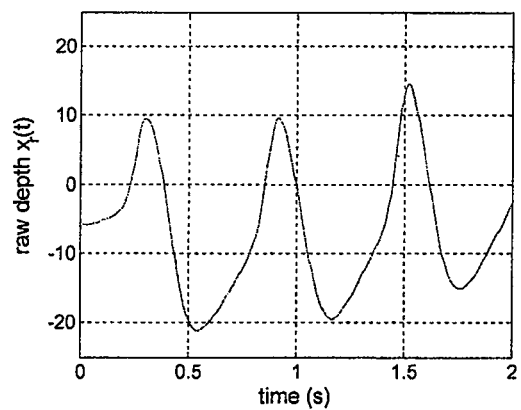
FIG. 2d shows the waveform of raw depth signal x_r(t) found by integrating chest speed according to an embodiment of the invention.

As will be explained below, the raw depth estimate signal x_r(t), as shown in FIG. 2d, is obtained by filtering and double integrating a received acceleration signal a(t). In one embodiment, the acceleration signal a(t) is measured by an accelerometer placed inside a CPR sensor unit that is applied on the sternum during compressions, and sampled at regular intervals. However, as will be clear to a person having ordinary skill in the art, other methods may be used to determine the acceleration signal a(t). FIG. 2a shows a typical waveform of a measured acceleration signal.

At step 110 of flow chart 100, the measured acceleration signal is first filtered by one or more digital filters to remove unwanted signal components, such as offset drift and/or high frequency noise. For instance, in one embodiment a comb filter is used to remove unwanted signal components. A comb filter is a very simple infinite impulse response filter. FIG. 2b shows the waveform of the acceleration signal in FIG. 2a filtered by a comb filter.

At step 112, the filtered acceleration signal is then double integrated. In one embodiment, the filtered signal is double integrated by an integrating digital filter. As will be clear to persons having ordinary skill in the art, the order of the filters will not influence the final result, and hence, the sequence of filtering and integration can be interchanged. FIG. 2c shows the waveform of chest speed found by integrating the filtered acceleration signal, and FIG. 2d shows the waveform of raw depth signal x_r(t) found by integrating chest speed.

Filtering with a digital filter is a powerful and well-known technique for removing high frequency noise and/or drift from a digitized signal waveform. Digital filters can be tailored to different types (high-pass, low-pass, band-pass, band-stop), families (e.g., finite impulse response (FIR) or infinite impulse response (IIR)), and properties, such as order, phase, ripple and cut-off/corner frequencies.

Figure 2E:
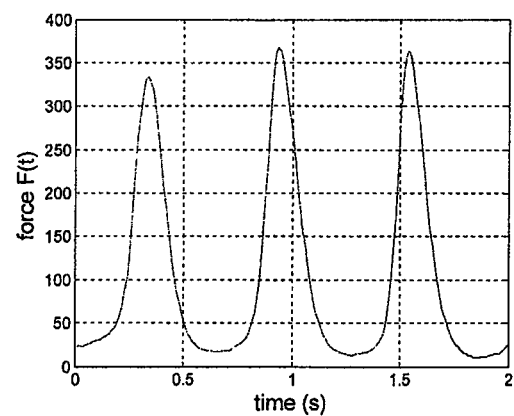
FIG. 2e shows the waveform of a compression force F(t) measured by a force sensor according to an embodiment of the invention.
Figure 2F:
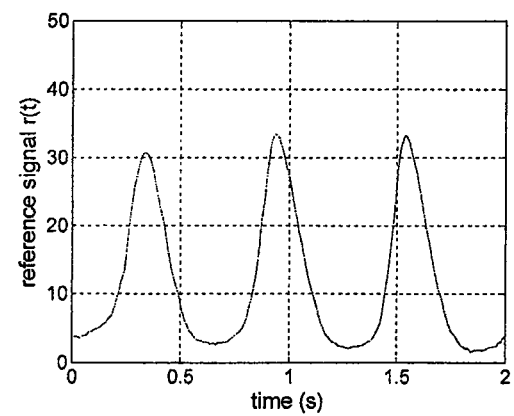
FIG. 2f shows the waveform of a reference signal r_f(t) according to an embodiment of the invention.

Now turning to calculating the compensation signal x_c(t). The compensation signal is calculated by subtracting a reference signal r(t) from a filtered reference signal r_f(t). FIG. 2f shows the waveform of a reference signal r(t). At step 120 of flow chart 100, the reference signal r(t) is produced from an independent reference signal R(t) by adjusting the independent reference signal R(t) to have a similar amplitude, shape and phase as the raw depth signal x_r(t). In one embodiment, the reference signal r(t) is deduced from measurements generated by a force sensor measuring compression force. The sensor, which may be situated between the palm of the hand of the rescuer and the victim's chest, samples force F(t). In one embodiment, the sensor samples force F(t) synchronously with the accelerometer sampling. FIG. 2e shows the waveform of a compression force F(t) measured by a force sensor. Other types of reference signals that can be used include ECG, thoracic impedance measurements with compression-related artifacts, or various kinds of blood pressure measurements. The independent reference signal R(t) may also comprise a combination of any information producing signals. For instance, in one embodiment the reference signal R(t) is a combination of two or more of the signals mentioned above.

Typically, since the output signals from different types of sensors have different units and thus different amplitudes, the numerical amplitude of the independent reference signal R(t) may need to be adjusted as in step 122. The numerical amplitude of the independent reference signal R(t) may be adjusted to approximately match the numerical amplitude of the depth signal x(t). In addition, the reference and depth signals may also have a phase difference or delay which may need to be adjusted for. These adjustments may be produced by calculating the difference in phase and amplitude ratio of the independent reference signal R(t) and a previously determined compression depth signal x(t−1).

The relationship between the independent reference signal R(t) and the phase/amplitude adjusted reference signal r(t) will be further explained by an example. Assume using a compression force F(t), where a reference signal gives R(t) =F(t). The force is measured in Newtons and the depth in mm. Thus, the relationship between force amplitude in N and the depth amplitude in mm is known. However, due to a viscous force component in the chest, depth usually is delayed in relation to force. Thus, the phase of the amplitude-adjusted reference signal may need to be adjusted to better match with depth. FIG. 2f shows the waveform of a reference signal r(t) found by adjusting the amplitude and phase of the force signal F(t) in FIG. 2e to reasonably match the raw compression depth signal x_r(t).

The ratio of force to depth during compression has units of k (N/mm), where k is chest stiffness. Therefore, to calculate the reference signal r(t), the measured force F(t) must be divided by k, so that r(t)=F(t)/k. In one embodiment, the chest stiffness k is determined by simply dividing the maximum force of previous compressions with the corresponding maximum depth. The depth employed in this calculation can, for instance, be the depth x(t) of previous compressions as estimated by the algorithm. The phase difference of the force and depth signals may be determined by observing the difference in maximum and minimum points of previous compressions force F(t) and depth x(t). For the first compression(s), a constant value of k and μ can be used in order to start the calculation, where μ is chest damping. Depth can be absolute, such as measured relative to zero, or relative, such as measured relative to the previous point of lowest depth.

In another embodiment, the amplitude and phase of the force signal is adjusted by assuming the following relationship between a measured compression force signal F(t) and an adjusted reference signal r(t):

$$F(t)=kr(t)+\mu v(t),$$

or $$r(t)=(F(t)-\mu v(t))/k,$$

where v(t) is chest speed, k is chest stiffness and μ is chest damping.

Chest speed v(t) may be determined by differentiating x(t) or alternatively r(t) with respect to time. Both μ and k can be constants or variable with depth. As will be clear to a person having ordinary skill in the art, the equation above can further be generalized to include acceleration.

For the above described embodiments, the stiffness k and damping component μ, used to modify the amplitude and phase of the force signal, respectively, may, in one embodiment, be calculated as a function of depth from the waveforms of the force and depth for previous compressions. For instance, such methods have been described in, "*Compression force-depth relationship during out-of-hospital cardiopulmonary resuscitation*" by Tomlinson A, Nysaether J, Kramer-Johansen J, Steen P A, Dorph E. Resuscitation, 2006 (in press), or "*Anterior-Posterior Thoracic Force-Deflection Characteristics Measured During Cardiopulmonary Resuscitation: Comparison to Post-Mortem Human Subject Data Stapp Car Crash Journal*," Vol. 50 by Kristy B. Arbogast, Matthew R. Maltese, Vinay M. Nadkarni, Petter Andreas Steen, Jon B. Nysaether, November 2006, (in press), both of which are herein incorporated by reference in their entirety. In another embodiment, the values for k and μ used in the calculation of r(t) can be based on mean or median values of k and μ found for previous compressions.

Figure 2G:
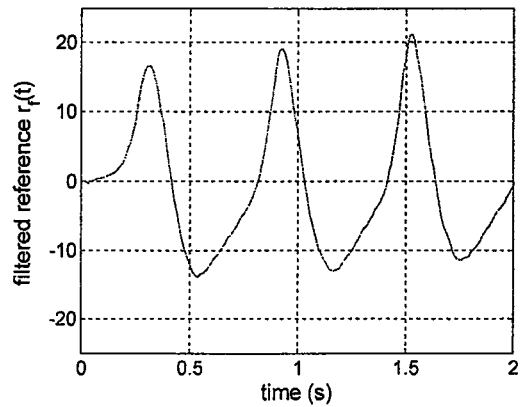
FIG. 2g shows the waveform of the reference signal after being filtered according to an embodiment of the invention.
Figure 2H:
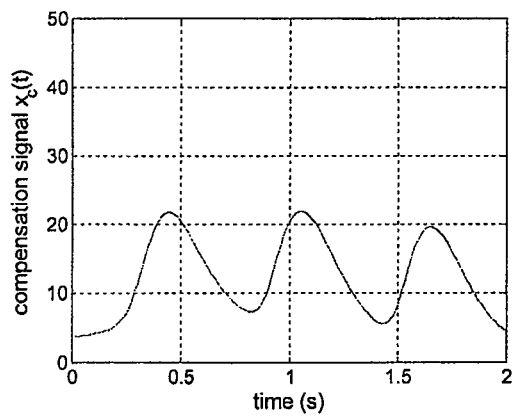
FIG. 2h shows the waveform of the compensation signal x_c(t) according to an embodiment of the invention.

At step 124 of flow chart 100, the reference signal r(t) is then filtered to get r_f(t). FIG. 2g shows the waveform of the filtered reference signal r_f(t). In one embodiment, the filters used to filter the reference signal are similar to those used to filter the acceleration signal. In another embodiment, the filters are not similar to those used to filter the acceleration signal, but result in a similar distortion as is found in the acceleration signal. At step 126, a compensation signal is obtained by subtracting the filtered reference signal r_f(t) shown in FIG. 2g from the original reference signal r(t) shown in FIG. 2f. The compensation signal x_c(t) thus, represents the portion of the reference signal that has been removed by the filters. A waveform of the compensation signal x_c(t) is shown in FIG. 2h.

Figure 2I:
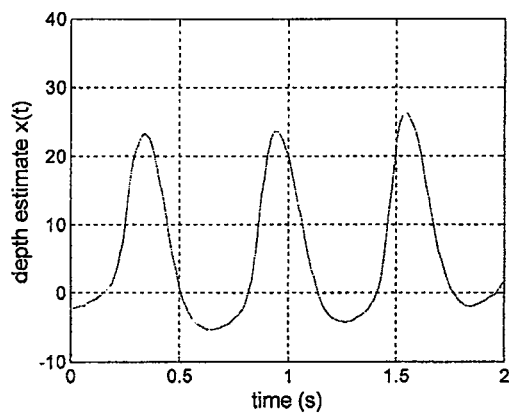
FIG. 2i shows the waveform of the estimate of depth x(t) according to an embodiment of the invention.

Therefore at step 128, the compression depth estimate signal x(t) may be calculated from the compensation signal x_c(t) and the raw compression depth signal x_r(t). FIG. 2i shows the waveform of the estimate of compression depth x(t) according to one embodiment of the invention. As will be clear to a person having ordinary skill in the art, the bottom points of the waveform x(t) may from time to time show significant offsets from zero. Thus, in general, the x(t) is more accurate in calculating the relative compression depth of each compression rather than the absolute compression depth of each compression. In one embodiment, to accommodate for this the depth output can be reset to zero after each compression, for instance at the point of minimum force or depth between two compressions. In another embodiment, in order to measure the absolute compression of the chest, the depth x(t) can be reset to a depth x0 after each compression, where x0=F_min/k. Here, F_min is the force at the point where depth is reset (Tomlinson et al., 2006).

It may be observed that the signal r(t), having similar amplitude, shape and phase as the compression depth signal x(t), is in itself an estimate of compression depth. Under special circumstances, for instance during transport when acceleration is influenced by the movement of the patient backing surface, r(t) may give a better estimate of compression depth than x(t). Thus, when such situations are detected, the system may choose to display r(t) instead of x(t) as a representative of compression depth.

In another embodiment, compression depth may be a hybridization of r(t) and x(t). For instance, one can let r(t) represent the shallowest part of the compression and x(t) the deepest part of the compression, and for instance let there be a gradual change from r(t) to x(t) in a predefined depth interval, for instance 10-20 mm depth.

All methods discussed above may be implemented from hardware and/or software. In one embodiment, the filtering, integrating, and adjustments to signals are performed by a processor. The accelerometer may be physically or wirelessly coupled to the hardware and/or software performing the methods discussed above. Similarly, the component or components that determine the independent reference signal may be physically or wirelessly coupled to the hardware or software operable to adjust and filter the independent reference signal.

As stated above, the sensor may be used on a manikin for the purpose of calculating chest compression depth during CPR training. The sensor may be used externally on a manikin chest as if it were a real patient, or be integrated into the manikin.

Although the present invention has been described with reference to the disclosed embodiments, persons skilled in the art will recognize that changes may be made in form and detail without departing from the spirit and scope of the invention. Such modifications are well within the skill of those ordinarily skilled in the art. Accordingly, the invention is not limited except as by the appended claims.

What is claimed is:

1. A method of determining, using a processor, chest compression depth during CPR being performed on a patient or manikin, comprising:

receiving an acceleration signal representing an acceleration value of the chest compression;
filtering the acceleration signal at least once;
double integrating the filtered acceleration signal;
receiving and adjusting an independent reference signal to produce an adjusted reference signal;
filtering the adjusted reference signal at least once to produce a filtered adjusted reference signal;
determining, using a processor operatively coupled to receive the double integrated filtered acceleration signal, the filtered adjusted reference signal, and the adjusted reference signal, a compensation signal by subtracting the filtered adjusted reference signal from the adjusted reference signal; and
determining, using the processor, the chest compression depth by adding the double integrated filtered acceleration signal and the compensation signal.

2. The method of claim 1 wherein the acceleration signal is measured by a chest compression sensor.

3. The method of claim 1 wherein filtering the acceleration signal and filtering the adjusted reference signal are performed using the same filter.

4. The method of claim 1 wherein the independent reference signal is adjusted to have a similar amplitude, shape and phase as the double integrated filtered acceleration signal.

5. The method of claim 1 wherein the reference signal and the acceleration signal are filtered by digital filters.

6. The method of claim 1 wherein the double integration is applied to the acceleration signal before the acceleration signal is filtered.

7. The method of claim 1 wherein at least one of filtering the adjusted reference signal and filtering the acceleration signal is performed using a comb filter.

8. The method of claim 1 wherein the independent reference signal is deduced from at least one of a force signal, an ECG signal, thoracic impedance measurements, and blood pressure measurements.

9. The method of claim 8 wherein the force signal is generated by a force sensor measuring compression force exerted during CPR.

10. The method of claim 9 wherein the force sensor is situated between the palm of a hand of a performer performing CPR and a chest of the patient receiving CPR.

11. The method of claim 1 wherein the independent reference signal is deduced from a combination of a force signal and other measured information producing signals.

12. The method of claim 1 wherein the adjusted reference signal is produced by calculating the difference in phase and amplitude ratio of the independent reference signal and a previously determined chest compression depth signal.

13. The method of claim 1 wherein the acceleration signal and the independent reference signal are synchronized.

14. A system for determining real time chest compression depth on a patient or manikin during CPR, comprising:
an accelerometer configured to measure acceleration of the chest compression of the patient or manikin and generate an acceleration signal corresponding thereto;
a force sensor configured to measure chest compression force and generate a force signal corresponding thereto; and
a processor configured to receive the acceleration signal and the force signal, the processor further configured to filter and integrate the acceleration signal, the processor configured to adjust the force signal and filter the adjusted force signal, the processor configured to calculate a compensation signal by subtracting the filtered adjusted force signal from the adjusted force signal, the processor configured to calculate the chest compression depth from the compensation signal and the filtered and integrated acceleration signal.

15. The system of claim 14 wherein the acceleration signal and the force signal are filtered by similar filters.

16. The system of claim 14 wherein the processor is further configured to use a comb filter for filtering at least one of the acceleration signal and the adjusted force signal.

17. The system of claim 14 wherein the processor is configured to adjust the force signal to have a similar amplitude, shape, and phase of the filtered and integrated acceleration signal.

18. The system of claim 14 wherein the processor is configured to synchronize the acceleration signal with the force signal.

19. The system of claim 14 wherein the force sensor is positioned between the palm of the hand of a person performing the CPR and the chest of the patient or manikin.

20. The system of claim 14 wherein the processor is configured to calculate the difference in phase and amplitude ratio of the force signal and a previously determined compression depth signal.

21. The system of claim 14 wherein the processor is configured to filter the acceleration signal before it is integrated.

22. The system of claim 14 wherein the processor is configured to integrate the acceleration signal twice.

* * * * *